United States Patent [19]

Long et al.

[11] Patent Number: 5,170,929
[45] Date of Patent: Dec. 15, 1992

[54] ULTRASONIC ADHESION/DEHESION MONITORING APPARATUS WITH ACOUSTIC TRANSDUCER MEANS

[75] Inventors: David C. Long, Wappingers Falls; Krishna Seshan, Beacon, both of N.Y.

[73] Assignee: International Business Machines Corporation, Armonk, N.Y.

[21] Appl. No.: 890,907

[22] Filed: May 29, 1992

[51] Int. Cl.⁵ .......................................... H01L 21/607
[52] U.S. Cl. .................................... 228/102; 228/104; 228/264; 228/9; 156/73.1; 156/378; 73/587; 73/588
[58] Field of Search ............... 228/102, 104, 110, 111, 228/180.2, 191, 264, 1.1, 9, 19; 156/73.1, 73.2, 378; 73/587, 588

[56] References Cited

U.S. PATENT DOCUMENTS

| | | | |
|---|---|---|---|
| 3,784,079 | 1/1974 | Spanjer | 228/1.1 |
| 4,040,885 | 8/1977 | Hight et al. | 156/378 |
| 4,373,653 | 2/1983 | Salzer et al. | 228/104 |
| 4,419,562 | 12/1983 | Jon et al. | 219/130.01 |
| 4,586,642 | 5/1986 | Dreibelbis et al. | 228/4.5 |
| 4,696,708 | 9/1987 | Keller et al. | 156/64 |
| 4,746,051 | 5/1988 | Peter | 228/1.1 |

FOREIGN PATENT DOCUMENTS

| | | | |
|---|---|---|---|
| 3429776 | 2/1986 | Fed. Rep. of Germany | 228/1.1 |
| 794488 | 1/1981 | U.S.S.R. | 228/104 |

OTHER PUBLICATIONS

Welding Design and Fabrication, "Acoustical Holography Looks Through Welds", William G. Ehlman, pp. 68-70, Feb. 1977.

J. R. Behun, et al., IBM Research Disclosure, Entitled: "Ultrasonic Method to Remove Chips Mounted on Ceramic or Other Materials Substrates" Aug. 1981 No. 328.

Primary Examiner—Samuel M. Heinrich
Attorney, Agent, or Firm—Ira David Blecker

[57] ABSTRACT

An ultrasonic adhesion/dehesion monitoring apparatus for monitoring the quality and/or adhesion/dehesion between first and second substrates comprising: (a) an ultrasonic source for transmitting ultrasonic energy to at least first and second substrates; (b) acoustic transducer means proximate to the ultrasonic source and/or the substrates; and (c) monitor means coupled to the acoustic transducer means for monitoring the ultrasonic signal from the ultrasonic source. Also disclosed is a method for monitoring the quality and/or adhesion/dehesion between first and second substrates in the ultrasonic adhesion/dehesion monitoring apparatus.

10 Claims, 4 Drawing Sheets

ULTRASONIC ADHESION/DEHESION MONITORING APPARATUS WITH ACOUSTIC TRANSDUCER MEANS

RELATED APPLICATION

This application is related to Long et al., "Ultrasonic Adhesion/Dehesion Monitoring Apparatus With Power Feedback Measuring Means", Ser. No. 07/890,988, filed May 29, 1992.

BACKGROUND OF THE INVENTION

This invention relates to ultrasonic apparatus primarily used for wire bonding but also used for various other processes such as semiconductor chip and input/output (I/O) pin removal. More particularly, this invention relates to an apparatus for monitoring the adhesion of the wire during bonding and the dehesion of a semiconductor chip and I/O pin during removal.

The process of ultrasonic bonding is well known. Briefly, in ultrasonic bonding, the bonding tool is caused to vibrate at ultrasonic frequency while the wire end is applied under pressure to the portion of the body to which electrical connection is to be made.

A recognized problem of ultrasonic bonding is that the bond quality can vary appreciably from bond to bond on a given substrate even where bonding machine settings are nominally identical. One very important factor involved in the bond quality is the bond strength. In some cases, low strength bonds can be identified visually such as where there are defects apparent. However, in most cases no estimation of the strength of the bond can be made without destructively pull or shear testing the bond. This is not very practical since all bonds cannot be tested and the few marginal bonds present a serious reliability problem. At the present time, there are no commercially available ultrasonic wire bonding apparatus having provisions for in-situ monitoring the bond quality and/or strength.

Hight et al. U.S. Pat. No. 4,040,885 discloses an apparatus for nodestructively monitoring the bonding quality of an of an ultrasonic bonding system by detecting the amplitude deviation of a vibrating bonding tool in the freely vibrating (no-load) condition and during the ultrasonic bonding operation. For this purpose, a piezoelectric transducer is mounted on the ultrasonic bonding tool to measure the amplitude of the bonding tip.

Jon et al. U.S. Pat. No. 4,419,562 discloses a nondestructive apparatus for monitoring the quality of a laser beam weld by positioning an acoustic sensor at a distance from the weld. The acoustic sensor measures acoustic emission signals from the workpiece during the welding process.

Dreibelbis et al. U.S. Pat. No. 4,586,642 discloses an apparatus for monitoring the bonding of a wire to a substrate. In this apparatus, changes in the inductive and capacitive rectangle of the wire are monitored during the bonding operation.

Salzer et al. U.S. Pat. No. 4,373,653 discloses an ultrasonic wire bonding apparatus which also nondestructively monitors the force required to separate the bonding tool from the wire after the bonding operation. A quartz crystal transducer mounted in the base of the tool is used for measuring the force. Keller et al. U.S. Pat. No. 4,696,708 is similar to Salzer et al. except that a load cell of uncertain variety is utilized to measure the total ultrasonic energy exerted by the ultrasonic bonding tool.

The current state of the art approaches to the problem have thus far failed to reliably distinguish bad bonds from good bonds. The present inventors have, therefore, proposed an apparatus to reliably detect in-situ when a good ultrasonic bond has been made as the bonding occurs.

The use of an ultrasonic apparatus to remove or debond parts is less well known. Behun et al., "Ultrasonic Method to Remove Chips Mounted on Ceramic or of Other Materials Substrates", Research Disclosure, No. 328 (Aug. 1991), the disclosure of which is incorporated by reference herein, discloses the ultrasonic removal of chips from a ceramic substrate. Basically, a chip remove stud is adhered to the backside of a chip. The chip has been previously joined to the ceramic substrate via solder controlled collapse chip connections. The chip remove stud is attached to the horn of the ultrasonic tool. Upon the application of ultrasonic energy and an upward force, the solder connections break and the chip becomes debonded or dehered.

A problem with this method of chip removal, as discovered by the present inventors, is that as more of the solder connections become broken, the chip begins to vibrate to a greater extent. This follows from the fact that as the solder connections become broken, a constant amount of ultrasonic energy is being applied to a decreasing number of solder connections. Consequently, when the last of the solder connections are broken, the chip abruptly debonds or deheres from the substrate with frequent damage to the chip and the substrate.

The present inventors, therefore, have proposed an apparatus to monitor in-situ the adhesion of the chip to the substrate so that upon detecting a lessening of such adhesion, the power to the ultrasonic tool can be lessened to alleviate the abrupt debonding or dehering of the chip from the substrate.

It should be understood that the terms dehere and dehesion mean the opposite of adhere and adhesion and indicate the debonding or separating of components from a substrate.

Similar considerations apply to the abrupt removal of I/O electrical connector pins from a substrate.

It is, accordingly, a purpose of the present invention to have a monitoring apparatus to reliably detect when a good ultrasonic bond, for example between a wire and a substrate, has been made.

It is another purpose of the present invention to have a monitoring apparatus that regulates and varies the ultrasonic power according to the current adhesion conditions so as to perform chip removal, pin pull and the like without undue harm to the substrate.

These and other purposes of the invention will become more apparent after referring to the following description considered in conjunction with the accompanying drawings.

BRIEF SUMMARY OF THE INVENTION

According to one aspect of the invention, there is disclosed an ultrasonic adhesion/dehesion monitoring apparatus for monitoring the adhesion/dehesion between first and second substrates comprising:

(a) an ultrasonic source for transmitting ultrasonic energy to at least first and second substrates;

(b) acoustic transducer means proximate to the ultrasonic source and/or the substrates; and (c) monitor means coupled to said acoustic transducer means for monitoring the ultrasonic signal from said ultrasonic source.

According to a second aspect of the invention, there is disclosed a method for monitoring the adhesion/dehesion between first and second substrates in an ultrasonic adhesion/dehesion monitoring apparatus comprising an ultrasonic source for transmitting ultrasonic energy to at least first and second substrates, the method comprising the steps of:

(a) placing acoustic transducer means proximate to the ultrasonic source and/or the substrates; and (b) coupling monitor means to said acoustic transducer means for monitoring the ultrasonic signal from said ultrasonic source.

DETAILED DESCRIPTION OF THE INVENTION

Figure 1:
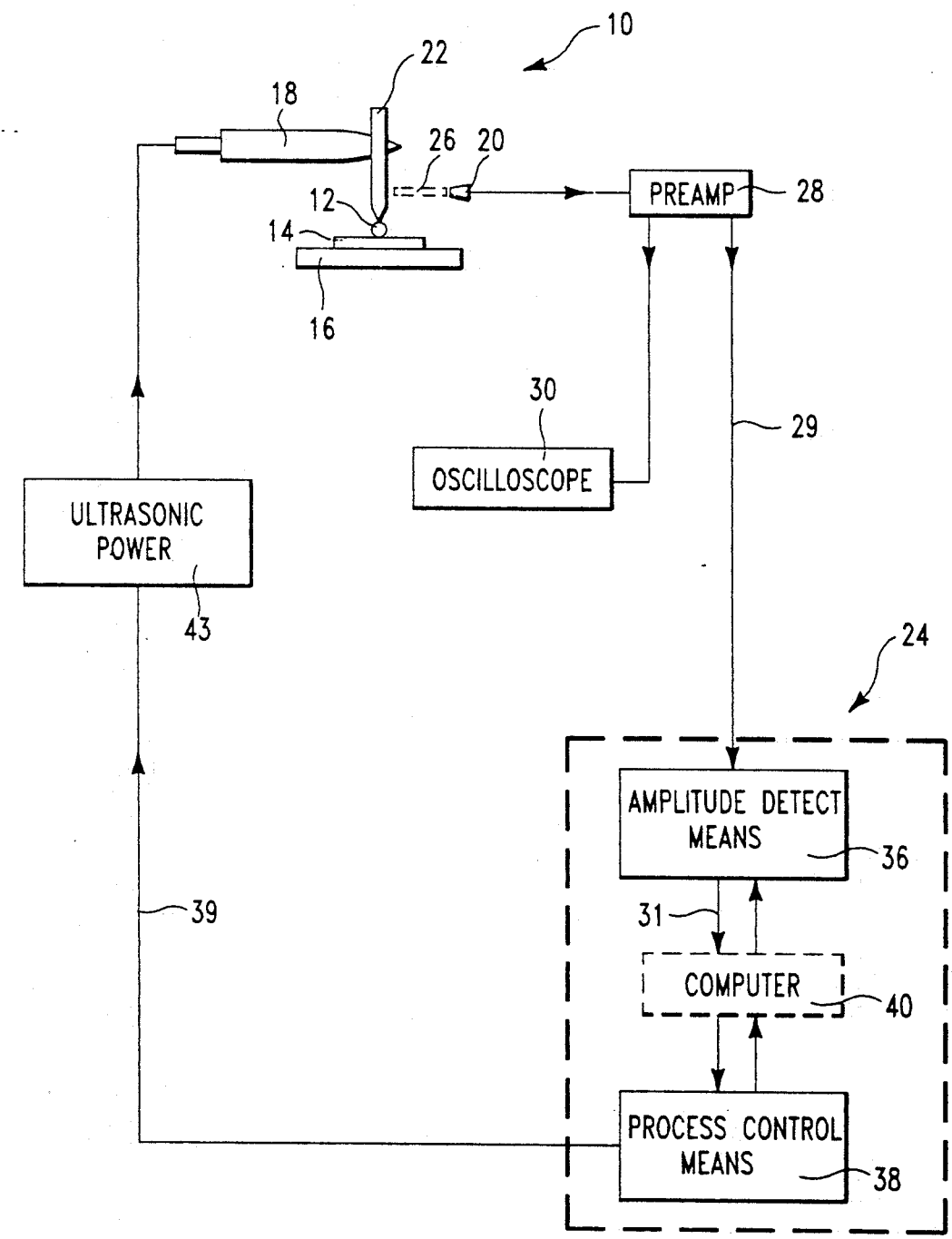
FIG. 1 is a schematic diagram of a first embodiment of the ultrasonic adhesion/dehesion monitoring apparatus according to the invention.

Referring to the Figures in more detail, and particularly referring to FIG. 1, there is shown an ultrasonic adhesion/dehesion monitoring apparatus, generally indicated by 10, for monitoring the adhesion/dehesion between first substrate 12 and second substrate 14. The first 12 and second 14 substrates are resting on fixture 16.

The apparatus 10 includes an ultrasonic source 18 for transmitting ultrasonic energy to the first 12 and second 14 substrates. As shown in the Figures, the ultrasonic source 18 is a transducer or horn vibrating at a frequency of about 60 kHz., which is typical for ultrasonic devices. The ultrasonic energy is directly transmitted to the substrates 12, 14 through a tip 22 or some other similar device. There must be some direct or indirect contact between the ultrasonic energy source and the substrates 12, 14 since the ultrasonic energy does not effectively travel through air for the purposes of the present invention. Further, there is an acoustic transducer means 20 proximate to the ultrasonic source 18 or substrates 12 and 14. As shown in FIG. 1, this acoustic transducer means 20 is a microphone which is sensitive to airborne ultrasonic frequencies since the purpose of the microphone is to pick up changes in the ultrasonic signal that are responsive to the adhesion or dehesion condition of the substrates 12, 14. In conjunction with acoustic transducer means 20 will be preamp. 28, which may be integral with the acoustic transducer means 20 or may be a separate unit. A Radio Shack electret microphone with integral preamp (Model 270-090) has been found to work satisfactorily for the purposes of the present invention.

In a preferred embodiment of the invention, there is a tube resonator 26 interposed between the acoustic transducer means 20 and the substrates 12, 14. When the acoustic transducer means 20 is placed near the ultrasonic source 18, then the tube resonator 26 is interposed between the acoustic transducer means 20 and the ultrasonic source 18. The tube resonator 26 will have a particular length which is tuned to the ultrasonic frequency of the source 18. For example, for an ultrasonic source of 60 kHz., the tube resonator 26 should have a length of about 5.5 mm. It is believed that the tube resonator 26 will enhance the ultrasonic signals passing through, thereby effectively reducing background noise.

Finally, the apparatus 10 includes a monitor means, generally indicated by 24, that is coupled to the acoustic transducer means 20. The monitor means 24 monitors the ultrasonic signal from the ultrasonic source 18.

Figure 4:
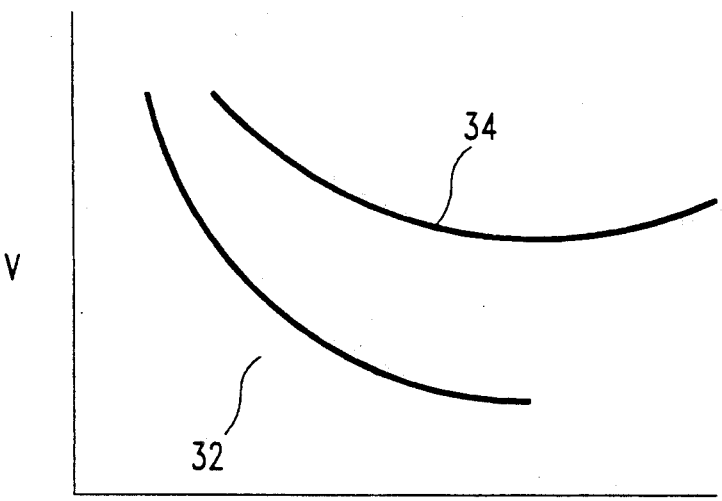
FIG. 4 is a diagrammatic representation of the acoustic signal detected during wire bonding.

The output from preamp. 28 is fed to oscilloscope 30 and/or monitor means 24. The present inventors have found the oscilloscope 30 useful for monitoring the signal from ultrasonic adhesion/dehesion monitoring apparatus 10. In one embodiment of the invention, substrate 12 is a wire and substrate 14 is a ceramic substrate and it is desirable to monitor the bonding of the wire to the substrate. Shown in FIG. 4 is the output from 2 wire bonding operations. In one operation, an engineering change wire was bonded to a metallic pad on the ceramic substrate with an ultrasonic frequency of 60 kHz. In the second operation, an engineering change wire was bonded at the same frequency to a metallic pad on a thin film layer of polyimide on the ceramic substrate. The output from preamp. 28 was fed to a Tektronix model 7834 oscilloscope 30. FIG. 4 is a diagrammatic representation of the signals viewed on the oscilloscope from the two bonding operations. Curve 32 represents the bonding on the ceramic substrate. When the curve reaches a predetermined minimum, a good bond has been achieved. Curve 34 represents the bonding on the ceramic substrate with the polyimide. Again, when the curve reaches a predetermined minimum, a good bond has been achieved. In this case, however, if bonding continues, the signal begins to rise indicating deterioration of the bond. While not wishing to be held to any particular theory, it is believed that after the initial good bond is formed, further bonding causes the polyimide to begin to tear, thereby effectively destroying the polyimide thin film layer.

The method of the present invention is thus useful for detecting when a good bond has been achieved and, further, is useful in preventing excessive bonding energy that leads to a deterioration of the substrate material.

Monitor means 24 provides a means for automating the monitoring and control of the apparatus 10. The output from preamp. 28 is fed to monitor means 24 which includes circuit means 36 for detecting a predetermined amplitude level of the ultrasonic signal. Also included is process control means 38 responsive to the predetermined amplitude level of the circuit means. Computer 40 may form a part of the process control means 38 or may be a separate unit. The output from process control means 38 is fed to ultrasonic power unit 43, which power is then regulated according to the signal received. If desired, the power may simply be turned on or off or varied to optimize the bonding conditions. Ultrasonic power unit 43 is typically powered by conventional AC power.

Figure 2:
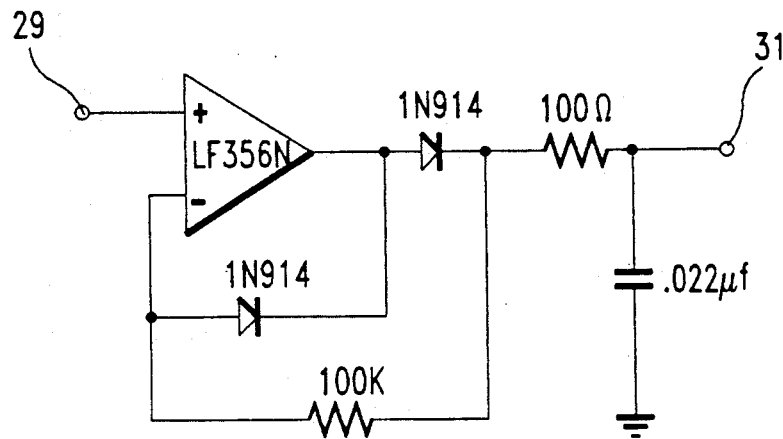
FIG. 2 is a circuit diagram of the amplitude detect means of the apparatus according to the invention.

A schematic diagram of a circuit for performing the function of the amplitude detect means 36 is shown in FIG. 2. Output 29 from preamp 28 is processed with resulting output 31 being generated. Amplitude detect means 36 is also called an envelope detector circuit with smoothing filter.

Figure 3A:
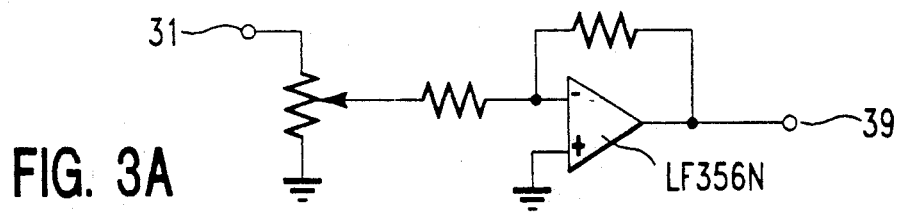
FIGS. 3A and 3B are schematic circuit diagrams of the process control means of the apparatus according to the invention.
Figure 3B:
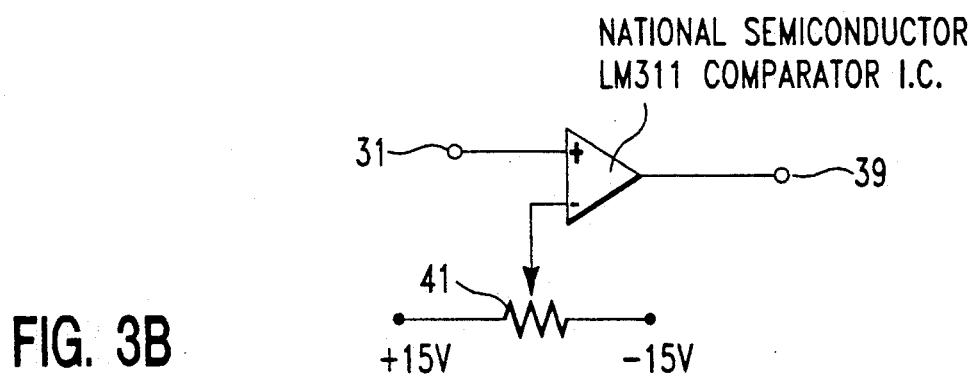

Shown in FIGS. 3A and 3B are schematic circuit diagrams of process control means circuits which are suitable for performing some of the functions of the process control means 38. FIG. 3A is a buffer amplifier which processes output 31 from the amplitude detect means 36 and generates an output 39 which varies the power of the ultrasonic power unit 42 in response to bonding or debonding conditions. FIG. 3B, on the other hand, is a comparator circuit which simply causes the power in ultrasonic power unit 42 to be turned on or off in response to bonding or debonding conditions. The variable resistor 41 acts as a trip level set point control to set the condition under which the power will be turned on or off.

Figure 6:
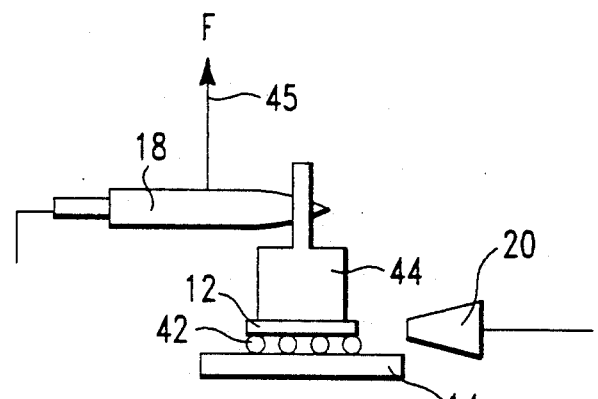
FIG. 6 is a schematic diagram of a second embodiment according to the invention as used for chip removal.

In another embodiment of the invention, as shown in FIG. 6, it is desired to monitor the dehesion condition during the removal of a chip from a substrate. In this case, substrate 12 is a chip and substrate 14 is a ceramic substrate. The chip 12 is adhered to the ceramic substrate 14 by solder balls 42. Stud 44 is adhered to the top of the chip 12 with Superglue cyanoacrylate adhesive, or some other fast drying adhesive. Upward force 45 is applied to horn 18. Ultrasonic energy is transmitted from horn 18 to stud 44 and then to substrates 12, 14. The ultrasonic energy causes the solder balls to fracture and, in conjunction with upward force 45, causes the separating of the chip 12 from the ceramic substrate 14. The dehesion of the chip 12 to the ceramic substrate 14 may be monitored by the apparatus according to the invention until the substrates 12, 14 become separated. The invention may also be practiced with other demountable components such as chip resistors, chip transistors, surface mount components, etc.

Figure 5:
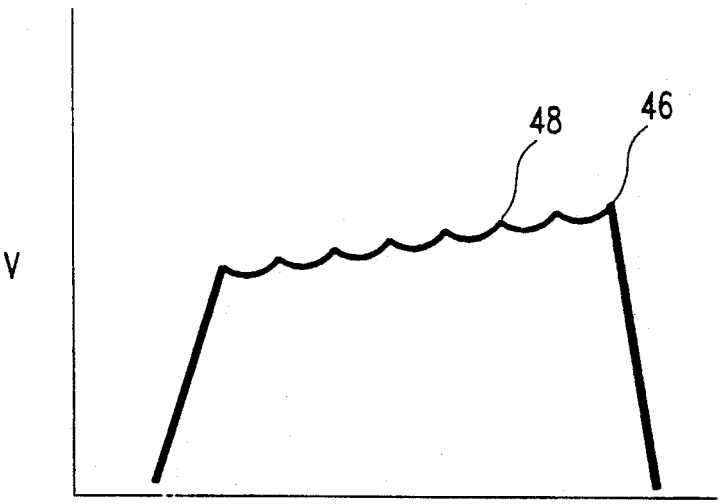
FIG. 5 is a diagrammatic representation of the acoustic signal detected during chip removal.

A diagrammatic representation of the signal viewed from oscilloscope 30 is shown in FIG. 5. The initial signal indicates that the substrates 12, 14 are adhered. As more energy is input to the substrates 12, 14, the solder balls 42 begin to fracture. Finally, at point 46 on the curve, the last of the solder balls 42 break and the substrates 12, 14 become separated, resulting in a sharp downslope of the curve. It is desirable, however, to ramp down the ultrasonic power 43 at point 48 before point 46 is reached to avoid the sudden dehering or debonding of the substrates 12, 14. By using oscilloscope 30, ramp down of the power may be accomplished manually. Alternatively, monitoring means 24 may do this automatically.

Figure 7:
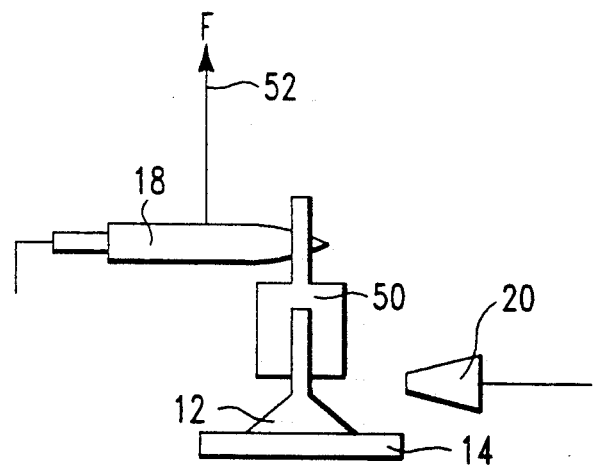
FIG. 7 is a schematic diagram of a third embodiment according to the invention as used for pin removal.

FIG. 7 illustrates a final embodiment of the invention. It is desired to monitor the adhesion of a pin (or a wire) being removed from a substrate. In this Figure, substrate 12 is an I/O pin and substrate 14 is a ceramic substrate. Pin 12 is attached to stud 50, for example by a fast drying glue, such as superglue cyanoacrylate adhesive or a clamping system (not shown), which is then connected to ultrasonic horn 18. Upon the application of ultrasonic energy and upward force 52, the pin 12 becomes separated from the ceramic substrate 14. The ultrasonic adhesion/dehesion monitoring apparatus according to the invention may be used to monitor the dehesion of the pin 12 to the ceramic substrate 14 and indicate when they are separated.

The embodiments shown in FIGS. 6 and 7 may also include a tube resonator as discussed with respect to the embodiment in FIG. 1.

The apparatus according to the invention will also function as a quality monitor in that the apparatus can also indicate if the wire, chip, pin or other component is poorly bonded to the substrate or if stud 50 is loosely attached to the horn 18 or if the glue or clamping system is loose.

It will be apparent to those skilled in the art having regard to this disclosure that other modifications of this invention beyond those embodiments specifically described here may be made without departing from the spirit of the invention. Accordingly, such modifications are considered within the scope of the invention as limited solely by the appended claims.

What is claimed is:

1. An ultrasonic adhesion/dehesion monitoring apparatus for monitoring the adhesion/dehesion between first and second substrates comprising:
   (a) an ultrasonic source for transmitting ultrasonic energy to at least first and second substrates;
   (b) acoustic transducer means proximate to the ultrasonic source and/or the substrates; and
   (c) monitor means coupled to said acoustic transducer means for monitoring the ultrasonic signal from said ultrasonic source.

2. The apparatus of claim 1 wherein said monitor means comprises circuit means for detecting a predetermined amplitude level of the ultrasonic signal and process control means responsive to said predetermined amplitude level of said circuit means for regulating the power of said ultrasonic source.

3. The apparatus of claim 1 wherein the first substrate is a wire and said apparatus monitors the bonding of said wire to the second substrate.

4. The apparatus of claim 1 wherein the first substrate is a chip, chip resistor, chip transistor or surface mount component, and said apparatus monitors the removal of said chip, chip resistor, chip transistor or surface mount component, from the second substrate.

5. The apparatus of claim 1 wherein the first substrate is a pin or a wire and said apparatus monitors the removal of said pin or wire from the second substrate.

6. The apparatus of claim 1 further comprising a tube resonator interposed between said acoustic transducer means and the substrates.

7. The apparatus of claim 1 wherein said acoustic transducer means is a microphone.

8. A method for monitoring the adhesion/dehesion between first and second substrates in an ultrasonic adhesion/dehesion monitoring apparatus comprising an ultrasonic source for transmitting ultrasonic energy to at least first and second substrates, the method comprising the steps of:
   (a) placing acoustic transducer means proximate to the ultrasonic source and/or the substrates; and
   (b) coupling monitor means to said acoustic transducer means for monitoring the ultrasonic signal from said ultrasonic source.

9. The method of claim 8 further comprising interposing a tube resonator between the acoustic transducer means and the substrates.

10. The method of claim 1 wherein said monitor means comprises circuit means for detecting a predetermined amplitude level of the ultrasonic signal and process control means responsive to said predetermined amplitude level of said circuit means for regulating the power of said ultrasonic source.

* * * * *